United States Patent [19]

Evans

[11] Patent Number: 4,834,707
[45] Date of Patent: May 30, 1989

[54] VENTING APPARATUS AND METHOD FOR CARDIOVASCULAR PUMPING APPLICATION

[76] Inventor: Phillip H. Evans, 1212 Benfield Dr., Dayton, Ohio 45429

[21] Appl. No.: 98,226

[22] Filed: Sep. 16, 1987

[51] Int. Cl.$^4$ ............................................. A61M 1/00
[52] U.S. Cl. .................................... 604/122; 604/126; 604/164
[58] Field of Search ................................. 604/48–53, 604/93, 122, 126, 104–109, 175, 164, 247, 264, 272, 170, 280, 283, 902; 128/632, 760, 763

[56] References Cited

U.S. PATENT DOCUMENTS

| | | | |
|---|---|---|---|
| 3,039,468 | 6/1962 | Price | 604/107 |
| 3,610,483 | 10/1971 | Visconti et al. | 604/48 |
| 3,776,239 | 12/1973 | Cooley | 604/122 |
| 3,893,448 | 7/1975 | Brantigan | 128/632 |
| 3,981,297 | 9/1976 | Dunn et al. | 128/632 |
| 4,014,317 | 3/1977 | Bruno | 604/247 |
| 4,069,826 | 1/1978 | Sessions et al. | 604/105 |
| 4,309,994 | 1/1982 | Grunwald | 604/284 |
| 4,493,707 | 1/1985 | Ishihara | 604/122 |
| 4,531,935 | 7/1985 | Berryessa | 604/53 |

OTHER PUBLICATIONS

Miller et al, "The Use of a Vent for the Left Ventricle . . . " Am. Col. of Surgeons; Surgical Forum (1953) vol. 4, pp. 29–33.
Jones et al; "A Vent Valve to Minimize Air Embolism . . . ,"; Jour. of Thoracic Surgi. (Aug. 1964) vol. 48, No. 2, pp. 310–313.

Primary Examiner—C. Fred Rosenbaum
Assistant Examiner—Mario Costantino
Attorney, Agent, or Firm—Richard C. Litman

[57] ABSTRACT

This device relates to an improvement on mechanical enhancement of the pumping action of the human heart, which is achieved by an external venting source, such as a pump joined to an instrument insertable into a patient's heart or aorta and serving to vent excessive gases from the heart, thereby improving brain and lung functions in a closed-loop fashion, by improving the pumping ability of the human heart.

2 Claims, 4 Drawing Sheets

VENTING APPARATUS AND METHOD FOR CARDIOVASCULAR PUMPING APPLICATION

FIELD OF INVENTION

The present invention relates, in part, to an apparatus and a method of operation associated therewith for a mechanical enhancement of the pumping action of the human heart. More specifically, this apparatus relates to a method for venting excessive gases away from the heart.

BACKGROUND TO THE INVENTION

Heretofore, there have been many attempts to improve conditions associated with heart problems. These have ranged from chemicals such as digitalis and diuretics to such devices as artificial valves and artificial hearts. The attempts over the years, however, do not appear to include the combined recognition of energy relationships, leakage of gas back into the ventricles, and the removal of gas as a means for improving the ability of a heart to pump liquid, that is, blood. This invention is directed toward obtaining and maintaining a stable heart condition with the present apparatus as a means for that objective.

The heart dynamics, or more specifically the dynamics of one side of the heart, have become analytically describable as a fluid flow dynamic process with an input flow, namely the return flow; an output flow; and a difference between the input flow and output flow representing the rate of change of the amount of fluid within the heart at a given time.

To relate to the present invention the fluid must be considered to contain both gas and liquid. By varying the amounts of the gas and liquid, changes in output flow can be produced. If, for example, some of the gas at the entrance to the aorta is allowed to repeatedly leak back through the aortic valve, between each pulsation the amount of gas within the heart can build up and be repeatedly pumped and leaked back.

As the amount of gas pumped becomes greater the amount of liquid pumped becomes less. If carried very far, this process leads to a significant reduction in liquid flow, and an instability type of condition follows, somewhat representative of a heart arrhythmia condition.

To some extent the above description parallels an analysis of fluid control apparatuses, such as for aircraft engine fuel control systems, as in each case, both contain input signals, flow in, flow out and the like. Also, to some extent the above parallels that of some engines, again input signals, flow in, and flow out as in a pumping action.

The heart action is basically that of a pump. Pumps work on an energy basis. When a pump is presented with a mixture of gas and liquid, the pump has a preference for operation on a minimal energy basis. Less energy is required to pump a given volume of a gas that to pump the same volume of a liquid.

Less energy is required to pump a given volume of gas through an orifice or restriction, and in the case of the heart, the orifice is the passage through a valve; both when the valve is properly open, and when the valve is damaged and supposed to be close but is actually partially open. If both a gas and a liquid are available, the heart has a tendency to preferentially pump a volume of gas; thus, decreasing the volume of liquid that can be pumped with a given amount of energy in a given amount of time.

If an outlet valve is damaged, in such a manner as to leak, there is a tendency for gas to leak back through the valve. The aortic valve, if damaged, can be such a valve. The gas can be preferentially pumped to the outlet side of the valve again and again, for a multitude of times.

The leaking of gas back through defective heart valves, the process being repeated, has as a ramification a decreasing amount of liquid, that is, blood, being pumped. This vapor/liquid ratio situation can be very bad with a defective heart just as with other forms of pumps, especially when the inlet pressure is very low even for very brief periods of time. In closed-loop systems, an improved capability in an active component, such as the heart in this case, can improve the overall performance of the loop.

An example of the aforementioned is the case in which heart performance is represented by a group of curves of pressure rise versus liquid volumetric flow rate with each curve represented by a different vapor/liquid ratio. Measurements may be in terms of weight flow rate or mass flow rate converted to liquid volumetric flow rate. Computerized regression methods are known and may be used to sort data, and perform related calculations, in such a manner as to describe the curves in terms of constant vapor/liquid ratio spaced in equal increments of vapor/liquid ratio. Curves can also be established for other parts of the closed-loop, such as the lungs. The combined oxygen absorption rate of the two lungs versus blood flow rate can be represented by a curve. In an analytical sense, there is a subtle but important factor involved in closed-loop systems herein explained. If component parts of the system, such as the heart and lungs, are described by the aforementioned curves, approximate transfer functions may be established for both open-loop and closed-loop performance. With such transfer functions it can be shown, as an approximation, that the closed-loop performance is related to the open-loop performance by a relationship of the following general form in Laplace transform notation:

$$\text{Closed-loop gain} = \frac{\text{Output}}{\text{Input}} = \frac{KG(s)}{1 + KG(s)}$$

*where $KG(s)$ represents the open-loop gain* note that dividing numerator and denominator by $KG(s)$ gives:

$$\frac{\text{Output}}{\text{Input}} = \frac{1}{\frac{1}{KG(s)} + 1}$$

The normal heart, as a component, represents substantial gain, in terms of power ratio, pressure ratio, and flow ratio. This is due to the ability of the heart to increase blood pressure and blood flow rate in normal operation. Excessive gas as described above substantially reduces such gain. In a close-loop system, the performance of a single component, e.g., the heart, may vary considerably from its curve of normal performance without a great effect upon closed-loop performance as indicated by closed-loop gain. For example, as a first order approximation, for an open-loop gain of 10 for a heart a departure from the curve of component performance will have only one-tenth as much effect on closed-loop performance as it does on open-loop performance, as indicated by the above equation. Although, the variable KG(s) can contain many factors representing the heart, lungs, arteries, veins, and the like—it is the heart that is a major factor with respect to gain— due to the pumping action. With this type of analysis, the amount of improvement expected for congestive heart failure by venting the gas can be estimated. Also, this type of analysis indicates that above normal or (superior) performance, such as for athletes, etc. is difficult to achieve.

This invention relates to those apparatuses and methods of venting to reduce the vapor/liquid ratio and thereby improve the capability of pumping liquid by the heart.

SUMMARY OF THE PRIOR ART

The following cited references, both published and patented, are are found to be exemplary of the U.S. prior art. They are:

| U.S. Pat. No. | Inventor |
|---|---|
| 4,625,712 | Wampler |
| 4,493,692 | Reed |
| 4,493,314 | Edwards |
| 4,385,637 | Akhavi |
| 4,385,950 | Pollak |
| 4,355,964 | Rodibaugh/Cobb |
| 4,397,049 | Robinson/Kitrilakis |
| 3,592,183 | Watkins et al |
| 3,995,617 | Watkins et al |
| 4,014,317 | Bruno |
| 4,309,637 | Akhavi |
| 4,309,994 | Grunwald |

The above cited references contain a variety of deaeration features, constructions of Self Priming Centrifugal Pumps, Gear Pump having Fluid Deaeration Capability, Hydraulically Actuated Cardiac Prosthesis With Three-Way Ventricular Valving and the like; however, the purposes of the above cited prior art are different from the present invention. Various constructions of pumps have been known to incorporate similar features, as the device disclosed herein, but such pumps have been related to applications other than the heart.

Another prior art reference is the article "Designing a Simulated Laboratory" by Niles Peterson, pages 286 through 296, June, 1984, Byte Magazine, published by McGraw-Hill, Inc., Peterborough, N.H. 03458.

The illustration on page 294 for the simulation of the Otto Frank experiment of the year 1896 is of interest as the present invention, and its utilization, involving dynamic closed-loop analysis and synthesis may be viewed as an improvement upon and a updating of the Otto Frank experiment.

One reference for closed-loop systems is the book "Automatic Feedback Control System synthesis" by John G. Truxal, 1955, McGraw-Hill Book Company, Inc. While closed-loop systems are not easily analyzed, the above book represents a relatively detailed and rigorous treatment of closed-loop techniques. Fortunately, as long as open-loop and closed-loop concepts are generally understood, a detailed knowledge of such things as transient response, frequency response, stability criterion and imaginary axis is not necessary for a general understanding of the invention.

These patents or known prior art uses teach and disclose various types of deaeration devices of sorts and of various manufacturers, and the like, as well as methods of their construction; but none of them, whether taken singly or in combination, disclose the specific details of the combination of the invention in such a way as to bear upon the claims of the present invention.

SUMMARY OF THE INVENTION

The primary object of the present invention is to temporarily improve the action of the heart so that other natural processes, usual medical treatments, and surgery can more effectively provide mending, healing and strengthening of the heart. Additionally, in conjunction with the above, the present apparatus is to be utilized to improve heart action when the usual methodology, such as major surgery, would otherwise be impractical as, for example, with the elderly.

A primary object of the invention is to obtain and maintain stable heart conditions by applying the device such that excessive gases, such as carbon dioxide and oxygen, are removed so as to effect a lower gas/liquid ratio in the bloodstream. The invention provides a method and apparatus for mechanical enhancement of the pumping action of the heart and improving conditions associated with heart problems, for example, congestive heart failure.

The apparatus has as its object the maintenance of a balanced ratio of vapor to liquid within the heart. A system of open-loop and closed-loop energy relationships, i.e., between the lungs and heart is utilized whereby a small percentage improvement in lung capacity is possible. The invention then becomes a tool by which a rebalancing of the system to new pressures, pulse rates, flows and so forth are involved as in automobile accident injuries or gunshot wounds, where excessive losses of blood have occurred.

Another object is to increase the flow of blood through the heart by decreasing the vapor/liquid ratio within the heart and the aorta.

A further object of the invention is to provide a means for the venting of excessive blood gases, excluding essential oxygen—especially that associated with red blood cells and hemoglobin—since some of the elements in the gases serve normal and necessary functions in the blood stream.

A yet further object of the invention is to function to vent gas in foam (i.e., air bubbles).

A still further object is to provide a construction for a venting means adaptable to use with animals (i.e., dogs, cattle) and the like.

A still further object is to provide reduced power requirements for an artificial heart such that the latter's power packs and the pacemaker itself may be made smaller.

These, together with other objects and advantages of the invention, reside in the details of the process and the operation thereof, as is more fully hereinafter described and claimed. References are made to drawings forming a part hereof, wherein like numerals refer to like parts throughout.

Brief DESCRIPTIONS OF THE DRAWINGS

DESCRIPTION OF THE PREFERRED EMBODIMENT

Figure 1:
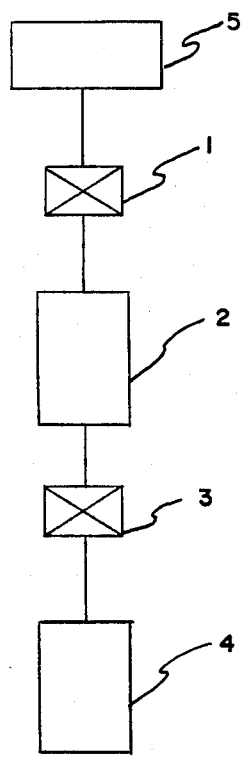
FIG. 1 is a block diagram in general form of the basic arrangement of one side of the heart and includes a designation of the location of the vent per one embodiment.

The system of FIG. 1 includes a section of a heart including a valve 1 at the outlet of ventricle 2 and a valve 3 between the ventricle 2 and atrium 4. This figure is generally illustrative purposes and includes a means of venting 5, such as a pump. This block diagram is applicable to the natural heart and to the artificial heart. The operation and use of the means of venting 5 are herein described below.

The heart is widely known to function basically as a pump and is highly efficient for its size. Comparing the amount of blood pumped per unit time, with the amount of energy used for such pumping, the amount of energy required to pump a given volume of a gas is less than the amount required to pump the same volume of liquid (i.e., blood). This can become very significant when gas accumulates in the heart. This gas can be contained in foam also. Gas can accumulate in the heart due to such factors as a defective valve as herein explained. The energy required for a given volume of gas to flow through an orifice is less than required for the same volume of liquid, i.e., blood, to flow through an orifice. The flow path through a defective heart valve constitutes such an orifice. In one sequence of events, the heart preferentially pumps gas more efficiently than liquid and, therefore, pumps some small volume of gas through the valve 1. During at least a portion of the pumping cycle some of the gas leaks back into the ventricle 2. Notice the energy relationships in both pumping and leaking of the ventricle 2, after the gas leaks back, it is preferentially pumped again. This type of process can be repeated with larger amounts of gas being pumped. Eventually, the amount of gas becomes so great as to adversely affect the amount of liquid, i.e., blood, that is pumped through the valve. The preferential pumping can be associated, at least in part, by the theoretic nature of liquids and gases, wherein; within a partially closed system, e.g., a heart ventricle and its correspondence valve, the density of gas is less than that of liquid, i.e., blood, such that the gas is disposed closer to the valve than is the liquid. This permits gas to be pumped before some of the liquid and leaving less time for the remaining liquid to flow through the outlet valve during each pulsation. Essentially, in this case, the muscle action on the liquid pushes the liquid against the gas, forcing the gas out first. Therefore, in this type of situation, more energy is also required from the muscle to pump a given amount of liquid, than in the case of a heart with a normal valve. This indicates a further reason why an increased amount of energy is required by the heart to pump a given amount of liquid. Consequently, for a given amount of energy the liquid pumping capability of the heart is reduced. With reduced liquid flow the ability to sweep gas away from the outlet side of the outlet valve is reduced, resulting in a greater leak back availability of gas. Consequently, the pumping of larger amounts of gas can occur. With gas flow into the inlet of the same side of the heart, the gas has to be pumped through in order to be in a position where it will leak back through the defective outlet valve, thereby being repumped through the outlet valve. In this case, the vapor to liquid ratio passing through the defective outlet valve affects the energy requirements for pumping a given amount of liquid. In addition, if a high vapor to liquid ratio is present at an inlet to the heart, additional energy is required to pump a given amount of liquid through the atrium and ventricle. Venting means 5 (such as a pump) is used to break up the above pattern of events so that the heart pumps more liquid. With this mechanical assistance, the performance of the heart is significantly improved. This can result in further improvements throughout the body; wherein the heart, lungs, brain, eyes, arteries, blood vessels, capillaries, and other organs throughout the body are operating, at least in part, as a combination of closed-loop systems.

Figure 2:
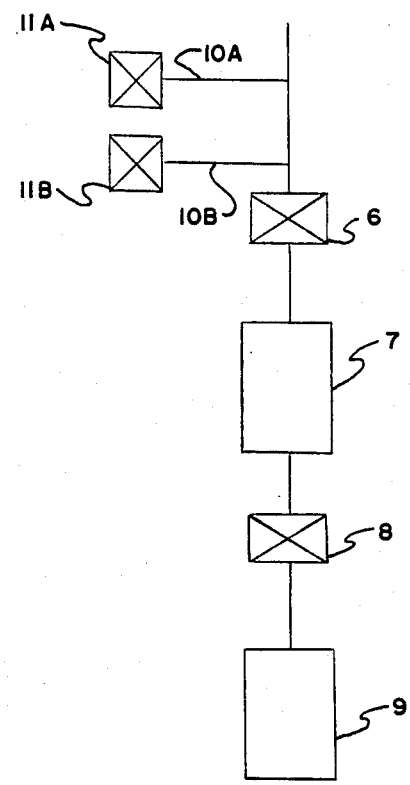
FIG. 2 is a block diagram for the left side of the heart and includes a designation of the location of the vent per the preferred embodiment.

The system shown in FIG. 2 is a descriptive illustration of FIG. 1. The aortic valve 6 is at the outlet of the left ventricle 7 and the mitral valve 8 is between the left ventricle 7 and the left atrium 9. The vent 10a and vent 10b, i.e., an elongated tubular instrument with a hollow needle-like housing, are used to vent gas. Operation and use of FIG. 2 is similar to FIG. 1 but is more specific with respect to the aortic valve 6, and the left ventricle 7. An example, of the application of FIG. 2, is the case of congestive heart failure. With a defective aortic valve 6 and malfunctions of the left ventricle 7, gas can be repeatedly pumped, adversely affecting the volume of liquid, i.e., blood, that can be pumped. One or more vents 10a and/or 10b may be used. The use of two vents offers advantages over one vent; namely: (1) Auxiliary means, in the event a vent becomes clogged; (2) If the pressure difference across the vent is very low it may be difficult to initiate vent gas flow; (3) Two vents offer the opportunity for more gas flow without increasing the flow cross-sectional area resulting in the removal of an excessive amount of liquid, blood, as well as gas. During the use of round vents, the diameter of the minimum cross-section of the flow passage is approximately 0.01 inch to 0.06 inch; with stop means 11a and 11b available to stop the flow through the vents in the event liquid flow becomes excessive. As seen in FIG. B, a knife-edged oval orifice 23 at the lower end of the needle-like housing with an internal diameter of approximately 0.02 inch at the opening to the vent and opening into an approximately 0.06 inch diameter flow passage would be advantageous to prevent clogging. The differential pressure across the knife-edged orifice 23, working on any material tending to plug the knife-edged orifice, would tend to keep the orifice open. A more complex embodiment could take the form of a more catheter-like configuration with gas venting provisions per this invention. Such an embodiment could include provisions for being inserted through any readily accessible vein. See FIG. 5, FIG. 8, and FIG. 10 for further details.

Figure 3:
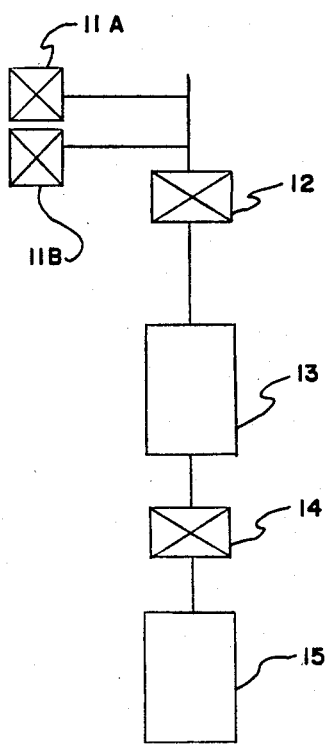
FIG. 3 is a block diagram for the right side of the heart and includes a designation of the location of the vent per another embodiment.

The system of FIG. 3 is for the right side of the heart and is similar to FIG. 2. A defective pulmonic valve 12, with or without a malfunctioning right ventricle, can result in an excessive amounts of gas being pumped. The amount of liquid, i.e., blood being pumped, is reduced. The relationships among energy, leaking, and pumping are similar to those explained in connection with FIG. 2. The operation and use of the venting instruments, hereinafter referred to as vent members 10a, and 10b, stop means 11a and stop means 11b are similar to the corresponding parts in FIG. 2.

Figure 4:
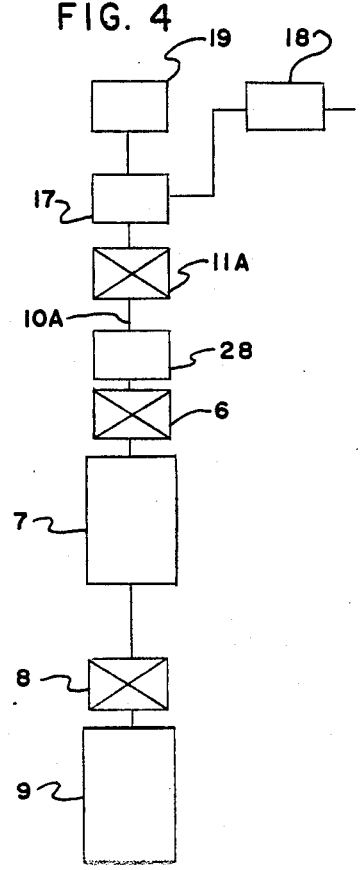
FIG. 4 is a block diagram with another embodiment incorporating a liquid-gas separator.

The system in FIG. 4 illustrates an alternative embodiment wherein a means of liquid-gas separation 17 connected to the stop means 11a. In this manner, guide element, said guide element having a plate for receiving a catheter 28, the stop means 11a, and the means of liquid-gas separation 17, are connected in a series, wherein the means of liquid-gas separation is used to assure that an excessive amount of liquid, i.e., blood, is not removed without being returned. The liquid can be returned to the blood stream via the return means 18. FIG. 4 also shows a vacuum means 19 such as a pump connected to the means of liquid-gas separation 17. The optional vacuum means 19 is used to expedite the removal of gas.

Figure 5:
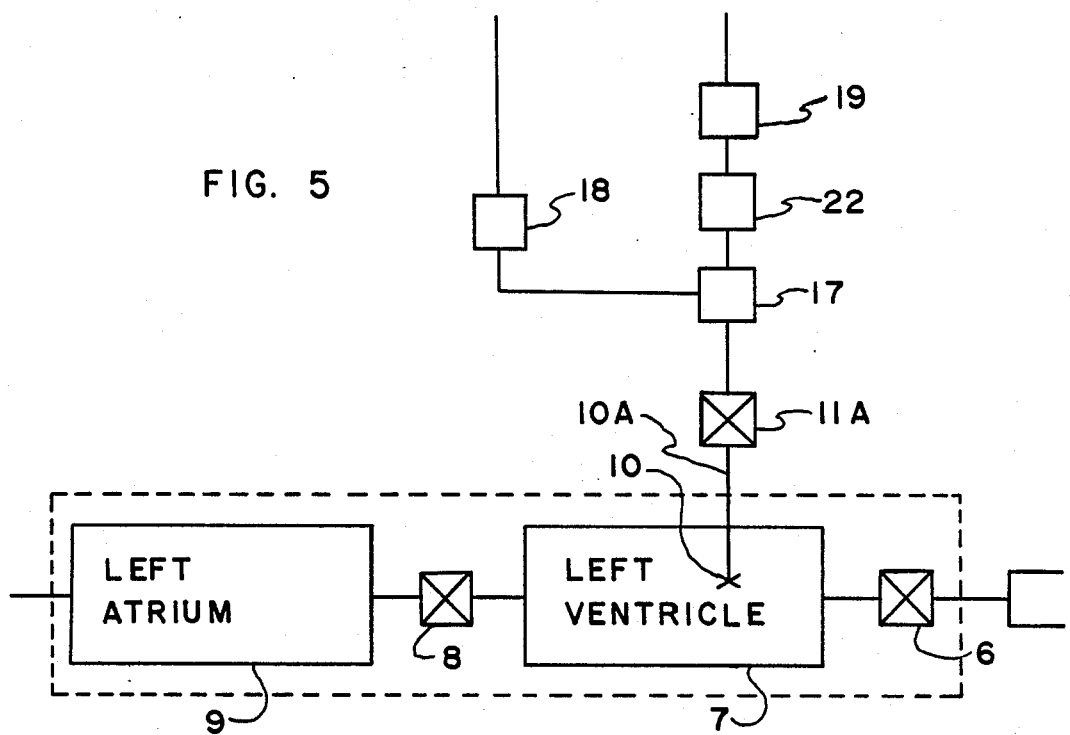
FIG. 5 is a block diagram of the preferred embodiment, and may be used in conjunction with the other figures for a better understand of this invention.

FIG. 5 depicts the apparatus in its preferred embodiment wherein, venting is done at the left ventricle L10 through vent member 10a. The vent member 10a is connected in series with stop means 11a. The stop means 11a is connected, in turn, to the means of liquid-gas separation 17 which is connected to both the return means 18 and check valve 22. The check valve 22, in turn, is connected to optional vacuum means or pumping device 19. The arrangement of FIG. 5 could be potentially significant with regard to application in connection with at least one form of congestive heart failure. Venting of gases as previously described is the significant function, especially in the case of a defective aortic valve. The affect of vapor to liquid ratio upon fluid flow capability is very pronounced, regarding an open-loop system with (1) a KG(s) term of a type representing a high ratio of heart outlet-pressure/inlet-pressure ratio and (2) a given amount of energy, as related to muscle capability. A high KG(s) term has an amplifying effect which makes the energy requirements highly sensitive to vapor/liquid ratio. Consequently, a much greater amount of energy is required to pump a given amount of liquid, when the amount of vapor at the inlet is large. Similarly, with a large amount of vapor in the atrium, a comparatively large amount of energy is required to pump a given amount of liquid. Decreasing the vapor/liquid ratio causes a relatively large improvement in liquid pumping capability with a given amount of energy from the muscle. A similar kind of situation with regard to pumping capability exists with excessive gas in the ventricle. As a result, venting of gas per this invention improves the vapor/liquid ratio and has a relatively large, or magnified, effect upon the liquid pumping capability of the heart. Furthermore, as indicated in FIG. 5 that venting per this method can be used as an alternative application, namely as a last resort, in removing a person off a respirator. In this alternative application the removal of gases, per this invention, helps to prevent an excessively high blood pressure by disallowing an excessive build up of the volume of gas and liquid within the heart. By preventing excessively high blood pressure, over a significant period of time, the respirator weaning process is improved.

Figure 6:
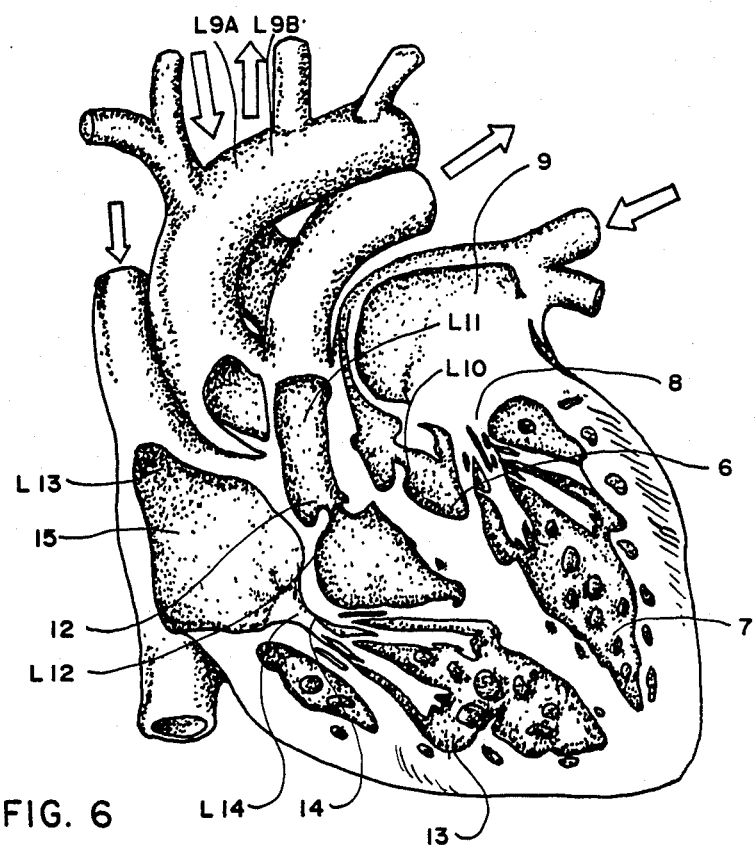
FIG. 6 is a pictorial cross-sectional diagrammatic representation of some of the material presented in FIG. 2 and FIG. 5 for the left side of the natural heart and designates some alternate vent locations.

FIG. 6 is a pictorial cross-sectional representation of the natural heart for the material presented in FIGS. 2 through 5. The venting members are placed in the locations as labeled. Vent location L9a and vent location L9b are indicated. Other vent locations are indicated by alpha-numeric designators L10, L11, L12, L13 and L14. Operation(s) and use(s) are as indicated in connection with descriptions of FIG. 1 through FIG. 10.

Figure 7:
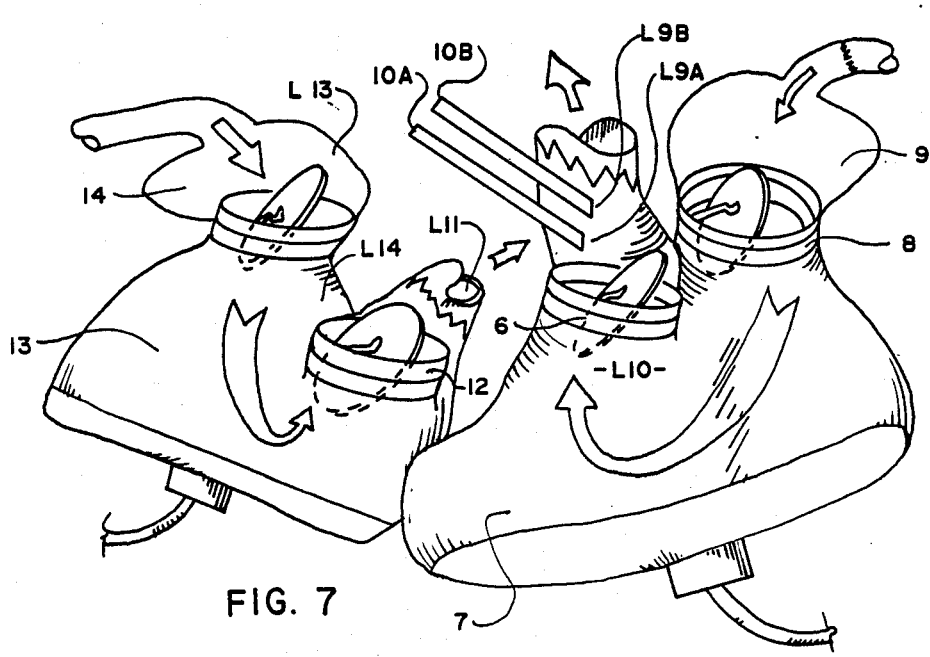
FIG. 7 is a pictorial diagrammatic representation of some of the material presented in FIG. 2 for the left side of a mechanical heart with a malfunctioning aortic valve and designates some additional venting locations.

FIG. 7 is a pictorial diagrammatic representation of an artificial heart in use with the apparatus FIG. 5. Parts are labeled with the same designations as the corresponding parts and locations in FIG. 6.

Comparatively, venting with respect to the natural heart and venting of the artificial heart type, it is apparent that a direct correlation lies between the two. Also, for a better understanding notice that the artificial heart acts as a pump and that venting per the invention can be demonstrated under carefully controlled laboratory conditions for a pump. By making parts of the pump or artificial heart of transparent materials, gas may be detected visually as evidenced by such items as bubbles, gas pockets, and foam. Pitting of one or more valves of the artificial heart or pump can be physical evidence of cavitation. Cavitation can also occur in the natural heart. Cavitation is likely to occur where there is decreased cross-sectional area in the flow passage, such as due to deposits; and when either the artificial or natural heart produces a pressure pulse with a high peak systolic pressure, the peak systolic pressure produces a high total pressure in the fluid which, in turn, produces a high velocity that results in a very low static pressure in the vicinity of the decreased flow area. The very low static pressure is produced in accordance with Bernoulli's principle and when gas bubbles are present there is a small region in the fluid in which the bubbles can expand and collapse violently, and, in the case of the natural heart, this violent action both irritates and damages the fluid passage surfaces, thereby possibly dislodging some of the latter's deposits.

Figure 8:
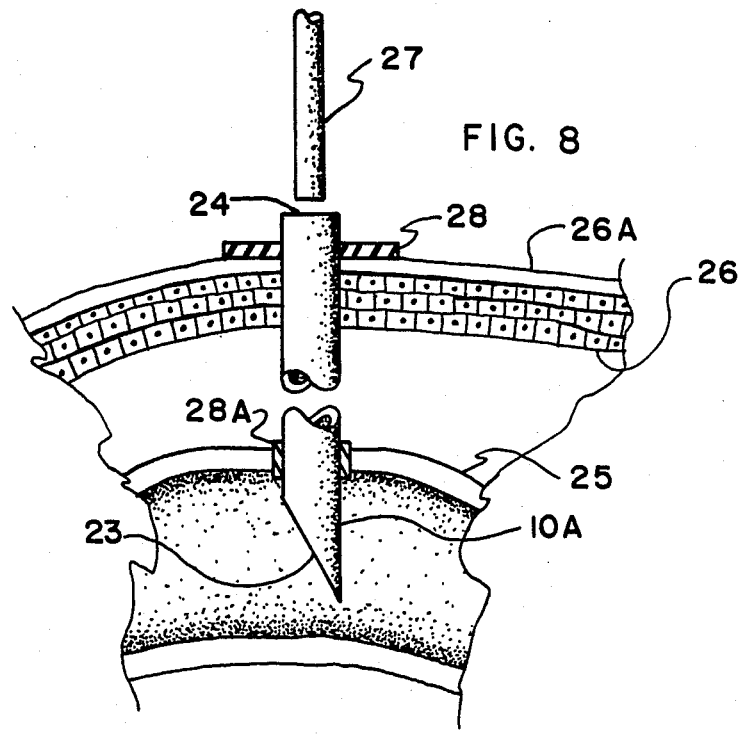
FIG. 8 is an enlarged view of a typical vent of FIG. 2.

FIG. 8 is an enlarged view of the venting member 10a of FIG. 2 and FIG. 5. Venting member 10b of FIG. 2 is essentially the same as 10a. The venting member 10a is fundamentally a hollow tube and has an aperture at tip 23 which is inserted into the aorta wall 25. As seen in the preferred embodiment of FIG. 5, the tip 23 of a catheter-type element is located inside the heart, e.g., the aortic wall 25. The hollow tube 24 extends through body wall 26 and skin 26a. The tube 24 is preferably somewhat flexible and made of implantable metal or plastic. The flexibility allows for movement of the heart and movement of the body. On a temporary or emergency basis, a large hypodermic needle may be substituted for the venting element 10a. Preferred dimensions are discussed in connection with FIG. 2. Preferably, the tip 23 is swaged and ground to form a small knife-edged oval orifice type aperture at the inlet of the tip. The removable guide means 27 is optional and serves as support means for the hollow tube 24 during insertion. A tube and tip slightly scaled up in size would permit faster venting and would be more sound structurally. Guide element 28 is used to attach the venting member 10a to the stop means 11a.

Figure 9:
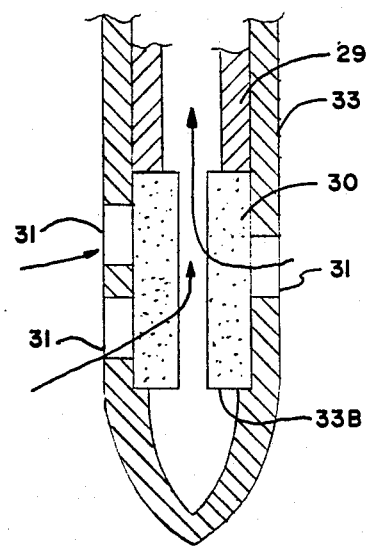
FIG. 9 is an enlarged view of a vent containing a porous insert allowing gases to flow out.

FIG. 9 is an enlarged view of an alternate form of the venting member 10a of FIG. 8. The major difference between FIG. 8 and FIG. 9 is the incorporation of porous insert 30, e.g., filter means, used to assure that gas, without an excess of blood, is vented. The porous insert 30 is removably attached within the outer housing 33 which corresponds approximately to venting member 10a of FIG. 8. The porous insert 30 is held in place between a rabbet-type fixture 33b and internal cylindrical sleeve 29. The gas is vented through orifice(s) 31, the porous insert 30, and internal cylindrical sleeve 29. The porous insert 30 may be made of porous metal, porous plastic, or porous ceramic. The porous insert 30 can be attached to internal cylindrical sleeve 29 to facilitate removal and replacement of the porous insert 30.

Figure 10:
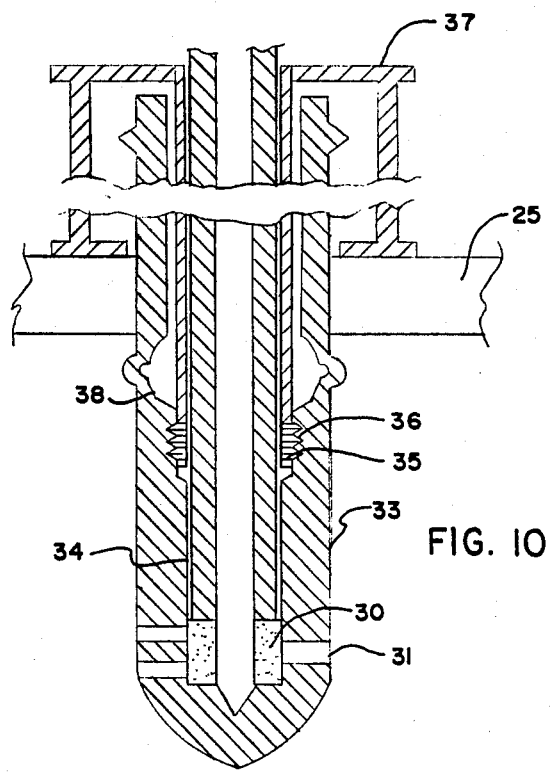
FIG. 10 is an enlarged view of an alternate vent showing apparatus for helping to retain a proper position, especially with respect to the inside of the heart.

FIG. 10 shows apparatus for helping to retain the orifice 31 inside the heart. The tightening rod 34 has a threaded end 35 which removably attaches to mating threads 36 in outer housing 33. The cap 37 is attached to the tightening rod 34. For an option to reduce the number of parts the internal cylindrical sleeve 29, the cap 34, and the tightening rod 34 can all be combined as a single unit. As the threads are tightened by rotating the tightening rod 34 relative to the outer housing 33, the cap 37 engages against the open end of the outer housing 33 and causes the housing to deform in the vicinity of preformed internal groove 38, forming retaining ridge 39. It is the function of retaining ridge 39 acting against the inner side of the heart wall 25 to help retain the end of outer housing 33 containing orifice 31 within the inside of the heart. To encompass locations such as vent location L9a and L9b of FIG. 2, the heart is defined so as to include the region of the aorta near the aortic valve.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications, and equivalents which may be resorted to, fall within the scope of the invention.

What is claimed is:

1. Apparatus for mechanically enhancing heart functions thereby improving conditions associated therewith, comprising in combination:
    an elongated hollow tubular housing having an inlet and an outlet and a tip adapted to puncture the skin;
    filter means within said housing adequate to permit the passage of gases and prevent the passage of liquids into said housing;
    flexible conduit means communicating with the interior of said housing for venting gases from the heart;
    said filter means being removably retained in said housing and replaceable without removing said housing tip from the skin;
    removable guide means within said flexible conduit means;
    attachment means for connecting pumping means to said flexible conduit means outside the skin to facilitate removal of gases; and
    stop means to halt flow through said flexible conduit;
    whereby to reduce the volume of gases pumped by the heart and increase the volume of liquid pumped.

2. Apparatus of claim 1 including a check valve in said flexible conduit means to prevent flow therethrough to the heart.

* * * * *